(12) United States Patent
Duncan et al.

(10) Patent No.: US 7,947,869 B2
(45) Date of Patent: May 24, 2011

(54) METHODS FOR INDUCING COTTON EMBRYOGENIC CALLUS

(75) Inventors: David R. Duncan, St. Charles, MO (US); Guangning Ye, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 222 days.

(21) Appl. No.: 12/117,398

(22) Filed: May 8, 2008

(65) Prior Publication Data

US 2008/0282432 A1 Nov. 13, 2008

Related U.S. Application Data

(60) Provisional application No. 60/916,802, filed on May 8, 2007.

(51) Int. Cl.
*C12N 15/82* (2006.01)
*C12N 15/87* (2006.01)

(52) U.S. Cl. ....................................... 800/278
(58) Field of Classification Search .......... 800/278, 800/314, 294, 205; 435/430.1, 468, 240
See application file for complete search history.

(56) References Cited

U.S. PATENT DOCUMENTS

| | | | |
|---|---|---|---|
| 4,672,035 A | 6/1987 | Davidonis et al. | 435/240 |
| 5,004,863 A | 4/1991 | Umbeck | 800/205 |
| 5,159,135 A | 10/1992 | Umbeck | 800/205 |
| 5,244,802 A | 9/1993 | Rangan | 435/240.5 |
| 5,583,036 A | 12/1996 | Rangan et al. | 435/999.999 |
| 5,695,999 A | 12/1997 | Rangan et al. | 435/427 |
| 5,986,181 A | 11/1999 | Trolinder et al. | 800/314 |
| 6,225,536 B1 | 5/2001 | Kasukabe et al. | 800/314 |
| 2004/0087030 A1* | 5/2004 | Armstrong et al. | 435/468 |
| 2005/0138693 A1 | 6/2005 | Duncan | 800/294 |

FOREIGN PATENT DOCUMENTS

| | | |
|---|---|---|
| WO | WO 89/05344 | 6/1989 |
| WO | WO 2004/006667 | 1/2004 |

OTHER PUBLICATIONS

Gamborg et al., "Nutrient requirements of suspension cultures of soybean root cells," *Exp. Cell Res.*, 50:151-158, 1968.

McCown et al., "Woody plant medium (WPM). A mineral nutrient formulation for microculture of woody plant species," *HortScience*, 16:453, 1981.

Murashige et al., "A revised medium for rapid growth and bioassays with tobacco tissue cultures," *Physiologia Plantarum*, 14:473-497, 1962.

Poon et al., "Improving the efficiency of embryogenesis in elite cotton cultivars," In: 11th Australian Cotton Conference Proceedings, Broadbeach, QLD, Australia, Aug. 10-12, 2004.

Potrykus, "Gene transfer to plants: assessment of published approaches and results," *Ann. Rev. Plant Physiol. Plant Mol. Biol.*, 42:205, 1991.

Qu et al., "Ectopic expression of the cotton non-symbiotic hemoglobin gene GhHb1 triggers defense responses and increases disease tolerance in arabidopsis," *Plant Cell Physiol.*, 47(8):1058-1068, 2006.

Reinbothe et al., "Jasmonate-induced proteins in cotton: immunological relationship to the respective barley proteins and homology of transcripts to late embryogenesis abundant (Lea) mRNAs," *J. Plant Growth Reg.*, 11:7-14, 1992.

Sakhanokho et al., "Putrescine enhances somatic embryogenesis and plant regeneration in upland cotton," *Plant Cell Tissue and Organ Culture*, 81:91-95, 2005.

Sun et al., "Brassinosteroid regulates fiber development on cultured cotton ovules," *Plant Cell Physiol.*, 46(8):1384-1391, 2005.

Tisserat et al., "Effects of ethephon, ethylene, and 2,4-dichlorophenoxyacetic acid on asexual embryogeniesis in vitro 1,2," *Plant Physiol.*, 60:437-439, 1977.

Trolinder et al., "Somatic embryogenesis in cotton (Gossypium). II Requirements for embryo development and plant regeneration," *Plant Cell, Tissue and Organ Culture*, 12:43-53, 1988.

Aydin et al., "Effects of brassinosteroid on cotton regeneration via somatic embryogenesis," *Biologica*, 61(3):289-293, 2006.

Firoozabady et al., Plant regeneration via somatic embryogenesis in many cultivars of cotton (gossypium hirsutum L.), *In Vitro Cell Dev. Biol.*, 29P:166-173, 1993.

Jin et al., "Identification of a novel elite genotype for in vitro culture and genetic transformation of cotton," *Biologica Plantarum*, 50(4):519-524, 2006.

Sakhanokho et al., "Induction of highly embryogenic calli and plant regeneration in upland (gossypium hirsutum L.) and pima (gossypium barbadense L.) cottons," *Crop Sci.*, 41:1235-1240, 2001.

Sun et al., "Somatic embryogenesis and plant regeneration from different wild diploid cotton (gossypium) species," *Plant Cell Rep.*, 25:289-296, 2006.

\* cited by examiner

*Primary Examiner* — Kent L Bell

(74) *Attorney, Agent, or Firm* — SNR Denton US LLP; Thomas P. McBride, Esq.

(57) ABSTRACT

Methods for the regeneration of cotton plants are disclosed. The use of novel compositions of media, media additives and new growth conditions during stages of development results in increased frequencies of embryogenesis, embryo maturation and embryo germination. The improved process results in higher production frequencies of transformed cotton plants.

18 Claims, No Drawings

METHODS FOR INDUCING COTTON EMBRYOGENIC CALLUS

This application claims the priority of U.S. Provisional application Ser. No. 60/916,802, filed May 8, 2007, the entire disclosure of which is incorporated herein by reference.

BACKGROUND OF THE INVENTION

1. Field of the Invention

The invention relates to methods for improving the efficiency of production of cotton plants. More specifically, novel compositions of media and incubation conditions for enhancing production of embryogenic callus and development of embryos are disclosed.

2. Description of Related Art

New technologies have allowed production of commercially viable transgenic crops and had significant economic impact on the agricultural industry. These advancements enable creation of new crop varieties containing desirable novel traits. For such traits to succeed in the market place, it is essential that the time to market be shortened as much as possible.

The development of genomics technologies has enabled identification and isolation of a large number of genes and has necessitated the need for reliable and efficient transformation production systems for testing the utility of these genes by transforming them into economically important crops such as cotton. Genetic engineering of plants is typically a multi-step process requiring transformation of plant cells and regeneration of transgenic plants. Plant cells are transformed by introducing a nucleic acid sequence that is typically integrated into the genome of the host cell; followed by regeneration of sexually competent plant from the transformed cells. In the case of cotton, this process typically includes steps of explant inoculation with *Agrobacterium*, undifferentiated callus formation, embryogenic callus induction, embryo induction, maturation and germination of embryo, and plant development.

Several methods are available for introducing nucleic acid sequences into plant cells and are well known in the art. Methods for transforming dicots primarily use *Agrobacterium tumefaciens* (reviewed in Potrykus, 1991). Transgenic plants reported include cotton (e.g. U.S. Pat. No. 5,004,863 and U.S. Pat. No. 5,159,135). These reports describe the overall regenerative process, including transformation and selection of a transformed plant tissue, induction of that tissue to form embryos, and germination of those embryos to form a plant. Various media compositions are reported to promote the process. However, embryogenesis has historically required several months or more.

U.S. Pat. Nos. 5,244,802, 5,583,036, and 5,695,999 disclose methods for regenerating cotton plants from somatic cells. Modified media compositions were reported to be useful at different stages of the regenerative process. More specifically, transformed plant tissue was grown in medium supplemented with glucose until phenolic secretions ceased, whereby the tissue was transferred to a medium supplemented with sucrose instead of glucose. Many of the cotton lines tested formed transgenic calli, but did not undergo embryogenesis and regenerate into a plant. U.S. Pat. No. 4,672,035 describes a process of regenerating cotton plants utilizing modifications in media composition.

The process of cotton transformation and regeneration of transformed cotton plants usually takes any where from 12 to 14 months. The major portion of this time is utilized in regeneration of cotton plants. Therefore, an unmet need exists in the art for improved methods for the transformation and regeneration of cotton plants. The present disclosure addresses such needs by providing improvements over published methods by reducing time or increasing efficiency for obtaining a cotton plant from cotton plant tissue.

SUMMARY OF THE INVENTION

In one aspect, the invention provides a method of improving the efficiency of cotton plant regeneration comprising the steps of: (a) culturing cotton plant tissue on non-embryogenic callus induction medium to produce a callus; (b) culturing the callus on embryogenic callus induction and embryo formation medium to produce an embryo; (c) culturing the embryo on embryo maturation medium to produce a mature embryo; (d) culturing the mature embryo on embryo germination medium; and (e) obtaining a regenerated cotton plant from the mature embryo; wherein the method further comprises at least one additional step selected from the group consisting of: adding a sucrose pulse step prior to culturing on embryogenic callus induction medium; culturing the cotton tissue in a medium containing a brassinosteroid; culturing the cotton callus and/or embryo in an atmosphere with altered air composition; culturing the cotton plant tissue in the presence of increased ethylene during step (a) in which callus induction takes place and without increased ethylene during steps (b-d) during which embryogenesis and embryo maturation takes place; culturing the callus and/or embryo at a temperature of from 30° C. to about 34° C.; culturing cotton plant tissue on non-embryogenic callus induction medium comprising ABA; and culturing cotton plant tissue on non-embryogenic callus induction medium that comprises calcium nitrate and potassium sulfate; reduced ammonium nitrate, calcium chloride, potassium nitrate, potassium iodide or cobalt chloride as compared to that found in MS medium; or enhanced cupric sulfate and manganese sulfate as compared to that found in MS medium; or no potassium nitrate.

In a certain embodiment, the cotton tissue is cultured on non-embryogenic callus induction medium that comprises calcium nitrate and potassium sulfate; reduced ammonium nitrate, calcium chloride, potassium nitrate, potassium iodide, and cobalt chloride as compared to that found in MS medium; and enhanced cupric sulfate and manganese sulfate as compared to that found in MS medium.

In certain embodiments, the method further comprises a step wherein the tissue comprises a cell that is transformed by a heterologous DNA sequence prior to step (b) or step (c). In particular embodiments, the transformed tissue or cell is selected on a medium comprising kanamycin, glyphosate, or glufosinate. In other embodiments, the method further comprises pre-soaking the tissue in a liquid medium for at least 1 hour prior to transformation. In certain embodiments, the liquid medium comprises the basal salt and carbohydrate components of MSO glucose medium. In yet other embodiments, the tissue is a cotton hypocotyl or cotyledonary explant.

In still yet other embodiments, the non-embryogenic callus induction medium comprises the basal salts component of WPSEL medium. In a particular embodiment, the non-embryogenic callus induction medium is WPSEL medium.

In certain embodiments the brassinosteroid is brassinolide. The method may further comprise culturing the cotton callus and/or embryo in a low oxygen environment, wherein the altered air atmosphere is supplemented with one or more gases selected from a group consisting of ethylene, nitrogen, and carbon dioxide.

Further, in certain embodiments the callus and/or embryo is cultured in a medium supplemented with one or more compound selected from the group consisting of: a brassinosteroid, ethylene, and an ethylene precursor.

In another aspect, the invention provides a method of improving the efficiency of cotton plant regeneration comprising the steps of: (a) germinating and growing a cotton seed under dark lighting conditions of about 0 µEinsteins $m^{-2}$ $sec^{-1}$ to less than about 5 µEinsteins $m^{-2}$ $sec^{-1}$ to obtain a cotton seedling comprising a hypocotyl; (b) excising the hypocotyl to obtain a hypocotyl explant; and (c) culturing the explant under conditions that lead to formation of embryogenic callus. In certain embodiments, the seed is germinated and grown under the dark lighting conditions for 2-4 days, followed by 1 day of growth under a light intensity of between about 20 µEinsteins $m^{-2}$ $s^{-1}$ and about 200 µEinsteins $m^{-2}$ $s^{-1}$, prior to hypocotyl excision. In a particular embodiment, the seed is germinated and grown under the dark lighting conditions for 2-4 days, followed by 1 day of growth under a light intensity of about 30 µEinsteins $m^{-2}$ $s^{-1}$, prior to hypocotyl excision. In certain embodiments, the dark lighting conditions comprise a light intensity of about 0 µEinsteins $m^{-2}$ $sec^{-1}$, or about 5 µEinsteins $m^{-2}$ $sec^{-1}$.

DETAILED DESCRIPTION OF THE INVENTION

The present invention provides improved methods for the regeneration of cotton plants from transformed and untransformed tissue. It yields particular benefits by reducing time of regeneration of cotton plant after transformation, and in increasing the efficiency of obtaining a quicker embryogenic response in a cotton callus culture. The improvements are accomplished through the control of environment and utilization of novel media compositions to enhance production of embryogenic callus and development of embryos. An improvement may be combined with one or more other treatment(s) as described below to yield additional or synergistic improvements in the level and timing of formation of cotton callus and embryogenic callus, somatic embryogenesis, embryo germination, and resulting cotton plants.

It has been found that alterations in cotton cell culture medium compositions, and in the environment of cotton cell cultures, allow for an early cotton embryogenic response. Thus, for instance, subjecting a cotton non-embryogenic callus cell culture to a "sucrose pulse" has been found to enhance subsequent cell growth and embryogenesis. Further, alternative cell culture media that comprise basal salts formulations distinct from those of Murashige & Skoog (1962; "MS Salts") have been found to promote embryogenesis when utilized at appropriate phases of the cotton cell culture growth process. In certain embodiments, salt formulations derived from those found in McCown & Lloyd's "Woody Plant Medium" (e.g. McCown & Lloyd, 1981) are found to enhance embryogenesis. In a particular embodiment, use of the basal salt formulation of LM Woody Plant Medium (WPM) (McCown and Lloyd, 1981) has been found to enhance cotton embryogenesis.

For instance, altered amounts or ratios of ammonium, nitrates, or other ions in a callus induction medium as compared to that found in media based on MS basal salts, may allow for enhanced embryogenesis and faster embryo maturation and plant regeneration. Without being bound by a particular theory, a comparison of MS basal salt and WPM basal salt components (Table 17) indicates that major differences between these compositions relate to the amount and source of nitrogen, calcium, potassium, sulfur, copper and cobalt. Thus, for instance, WPM basal salts comprise a lower level of nitrates than MS basal salts, and the nitrates, rather than being derived from ammonium nitrate and potassium nitrate, instead are derived from ammonium nitrate and calcium nitrate. There are overall fewer salts in WPM than in MS medium. The lower salt can reduce water stress on the tissue allowing for more rapid initial growth. Additionally, there is 4-fold more Ca in WPM than in MS, which may have regulatory effects. There is also 4-fold more sulfate in WPM than in MS medium. Sulfur has been identified, at least in alfalfa somatic embryo development, as needed for adequate embryo maturation. Finally, there is no KI or Co in WPM.

As noted above, certain embodiments of the present invention use an alternative basal salts formulation in the medium. For instance, media based on LM Woody Plant Basal Salts (e.g. Phytotech L-154; PhytoTechnology Laboratories, Shawnee Mission, Kans.) may be employed (e.g., "WPSEL"; see Table 13), instead of media based on MS basal salts (e.g., "UMSEL"; see Table 6) during the pre-embryogenic or non-embryogenic callus induction phase with or without a selection agent. The present invention provides for the use of modified basal salts components, e.g. as found in McCown woody plant medium (WPM), during various steps of the cotton cell culture process, including for instance substituting for the MS salts typically used during callus induction steps.

The present invention may use a basal salt medium for regeneration of cotton plant from transformed or non transformed cotton callus, supplemented with, for instance, Gamborg's $B_5$ vitamins, an auxin, a cytokinin, and a carbohydrate source, and referred to as a modified woody plant medium. For regeneration of a cotton plant from cotton callus, a plant tissue culture medium may be supplemented with one or more compounds selected from the group consisting of: a brassinosteroid such as brassinolide or other related polyhydroxylated steroid, an ethylene precursor, an auxin, a cytokinin, ascorbic acid, an ascorbic acid precursor, casein hydrolysate, and abscisic acid, among others. In one embodiment, MS Basal Salt medium supplemented with, for instance, a brassinolide, is used for regeneration of cotton plants from transformed or non-transformed cotton callus. Alternatively, a WPM-based basal salts medium may be supplemented with, for instance, brassinolide, for regeneration of cotton plants from transformed or non-transformed cotton callus.

In particular embodiments, one or more compounds including a brassinosteroid such as brassinolide or other related polyhydroxylated steroid, or an ethylene precursor may supplement the media used herein in order to enhance the efficiency and speed of regeneration of cotton plants from the described cotton cell cultures. These compounds may act on the cotton cells during any stage or stages of the procedure, for instance from excision of hypocotyl tissue, to transformation, callus formation or induction, induction of embryogenesis, maturation of embryos, germination of embryos, and growth of regenerated plants.

Furthermore, contrary to previous reports, ethylene is found to enhance embryogenesis and embryo maturation, when present at the appropriate stage in the cotton cell culture process. When added to pre-embryogenic callus, ethylene is found to aid subsequent embryogenesis, if it is removed prior to formation of embryonic tissues. Thus, ethylene, an ethylene precursor, or a compound that promotes ethylene synthesis may be added to pre-embryogenic cotton callus tissue, in order to promote subsequent embryo formation, while being removed from the medium or cell environment prior to embryo formation.

In yet another embodiment, the WPSEL-based medium may be supplemented with one or more additional ingredients as listed above, including for instance Gamborg's $B_5$ vitamins, an auxin, a cytokinin, and a carbohydrate source, and referred to as a modified woody plant medium, a brassinosteroid such as brassinolide or other related polyhydroxylated steroid, an ethylene precursor, ascorbic acid, an ascorbic acid precursor, casein hydrolysate, and abscisic acid, among others, to enhance embryogenesis and embryo maturation.

The described methods for enhancing cotton plant regeneration efficiency and speed may also be combined. Thus, a modified WPSEL-based basal salt component may be utilized along with, for instance, a brassinosteroid, an ethylene enhancing agent, or another medium or atmospheric supplement, growth condition, or alternative, to enhance regeneration. Pre-soaking of hypocotyl explants, for instance in liquid MSO glucose medium prior to a transformation attempt, was also found to enhance subsequent embryogenic callus formation.

A brassinosteroid, e.g. brassinolide, may be added to a cotton cell culture to enhance embryogenesis and embryo maturation. Thus, in certain embodiments, the presence of a brassinosteroid such as brassinolide at a concentration of about 2 μM to about 100 μM during embryogenic growth of callus is found to increase both the number of embryos formed, as well as the number of embryos exhibiting a more developed morphology, such as torpedo stage embryos. Growth of the cotton cell culture in a low oxygen environment (e.g. about 9% $O_2$ instead of 21% $O_2$) further enhances the effect of brassinolide in promoting embryogenesis. In particular embodiments, 5-50 μM brassinolide may allow for this effect.

An agent that enhances ethylene levels in the environment of a cotton tissue culture may include ethylene itself, or a substance that enhances ethylene synthesis, for instance such as the ethylene precursor 1-aminocyclopropane-1-carboxylic acid (ACC), or ethephon. When present during pre-embryogenic callus formation, ethylene enhances subsequent embryogenic callus formation of either transformed or untransformed cotton cells, if removed prior to the start of embryogenesis. In certain embodiments, the presence of ACC during callus formation (i.e. pre-embryogenesis growth such as on UMSEL medium) at a concentration of, for instance, 0.01 mM-1 mM results in enhancement of subsequent embryogenesis. In other exemplary embodiments, the presence of ACC at a concentration of about 10 to 150 μM during cotton callus growth on WPSEL medium, or medium with similar basal salts composition, results in enhanced formation of embryogenic callus during subsequent embryogenic growth.

According to the present disclosure "callus" refers to an undifferentiated proliferating mass of cells or tissue in vitro. Similarly "embryogenic callus" refers to a type of callus capable of differentiating into somatic embryos. "Non-embryogenic callus" refers to a type of callus composed of undifferentiated, often highly vacuolated cells that have not yet undergone embryogenesis.

"Non-embryogenic callus induction medium" or "pre-embryogenic callus induction medium" refers to a medium used to promote formation of non-embryogenic callus. "Embryogenic callus induction medium" refers to a medium used to promote formation of embryogenic callus. "Embryo formation medium" refers to a medium used to promote the formation of somatic embryos from embryogenic callus tissues. "Embryo maturation medium" refers to a medium used to promote the development and maturation of somatic embryos. "Embryo germination medium" refers to a medium used to promote the germination of somatic embryos, and the development of roots, shoots, and ultimately plants.

The term "transformation" refers to a process of introducing an exogenous nucleic acid sequence (e.g., a vector, a recombinant nucleic acid molecule) into a cell or protoplast in which that exogenous nucleic acid is incorporated into a chromosome or is capable of autonomous replication. By "exogenous" or "heterologous" is meant a nucleic acid molecule which originates from outside the plant cell into which the molecule comprising the nucleic acid sequence is introduced.

To initiate a transformation process in accordance with the present invention, it is necessary to construct a recombinant nucleic acid vector. "Vector" refers to a plasmid, cosmid, bacteriophage, or virus that carries exogenous DNA into a host organism. "Transformation Vector" therefore will define a vector that is capable of transforming a plant cell or plant tissue. Sometimes transformation vectors are also referred as recombinant nucleic acid vectors. Essentially a transformation vector comprises one or more expression units or cassettes comprising: a 5' promoter, an optional 5' non-translated sequence, a coding sequence or other nucleic acid sequence of interest (e.g., having agronomic utility), a polyadenylation signal. The coding sequence may be for a gene of interest or for a marker gene. The marker gene may be selectable or screenable. In essence, transformation or recombinant nucleic acid vectors comprise the regulatory elements sufficient for transcription of one or more desired mRNA in a plant cell. One or more expression units are usually flanked with at least one T-DNA border region which facilitates the transfer of the expression unit into a plant cell. Methods for preparing a plant transformation vector are well known in the art.

With the construction of the plant transformation vector or construct, the recombinant nucleic acid vector may be introduced into a suitable host such as *Escherichia coli* and mated into another suitable host such as *Agrobacterium*, or alternatively, directly transformed into competent *Agrobacterium*. These techniques are well known to those of skill in the art and have been described for a number of plant systems, including cotton (U.S. Pat. Nos. 5,004,863 and 5,159,135).

The use of *Agrobacterium* to introduce DNA sequences into plant cells is well known in the art (Fraley et al., 1987; Rogers et al., 1987a). Furthermore, the integration of the T-DNA is a relatively precise process, resulting in few rearrangements. The DNA sequence being transferred is defined by border sequences that enable the intervening DNA sequence to be inserted into the plant genome.

*Agrobacterium* transformation vectors are capable of replication in *Escherichia coli* as well as in *Agrobacterium*, thereby allowing for convenient manipulations (Klee et al., 1985). Moreover, recent technological advances in the structure of the vectors have simplified the process of inserting a specific DNA coding sequence into the vector in a suitable orientation. The structural improvements of these vectors comprise a convenient multi-cloning region containing multiple restriction sites, a flanking 5' promoter region, and a 3' polyadenylation site. The gene of interest is ligated into the multi-cloning site and is thus operably linked to the necessary 3' and 5' regulatory elements (Rogers et al., 1987b). In addition, *Agrobacterium* containing both armed and disarmed Ti genes can be used.

There are many variations of these types of vectors, and any that contain the necessary elements for producing mRNA from an inserted DNA coding sequence in a plant cell are suitable for participation in the invention. In those plant species where *Agrobacterium*-mediated transformation is efficient, the use of *Agrobacterium* is preferred due to the facile and defined nature of the gene transfer.

The present invention encompasses the use of bacterial strains to introduce genes into cotton plants. Besides *Agrobacterium* sp., other bacterial strains can also be used to transform cotton cells. For example, bacteria from genus *Rhizobium* can also be used for transforming cotton plant cells. Isolates and species of *Rhizobium* that can be used to practice present invention include: *Rhizobium* sp., *Rhizobium* sp. NGR234, *Rhizobium leguminosarum* Madison, *R. leguminosarum* USDA2370, *R. leguminosarum* USDA2408, *R. leguminosarum* USDA2668, *R. leguminosarum* 2370G, *R. leguminosarum* 2370LBA, *R. leguminosarum* 2048G, *R. leguminosarum* 2048LBA, *R. leguminosarum* bv. *phaseoli*, *R. leguminosarum* bv. *phaseoli* 2668G, *R. leguminosarum* bv. *phaseoli* 2668LBA, *R. leguminosarum* RL542C, *R. leguminosarum* bv. *viciae*, *R. leguminosarum* bv. *trifolii*, *Rhizobium etli* USDA 9032, *R. etli* bv. *phaseoli*, *Rhizobium tropici*, *Mesorhizobium* sp., *Mesorhizobium loti* ML542G, *M. loti* ML4404, *Sinorhizobium* sp., *Sinorhizobium meliloti* SD630, *S. meliloti* USDA1002, *Sinorhizobium fredii* USDA205, *S. fredii* SF542G, *S. fredii* SF4404, *S. fredii* SM542C, *Bradyrhizobium* sp., *Bradyrhizobium japonicum* USDA 6, and *B. japonicum* USDA 110. In a particular embodiment, *Agrobacterium tumefaciens* is utilized for the transformation. *A. tumefaciens* strains may include nopaline strains such as C58; octopine strains such as LBA4404; and agropine strains such as EHA105, EHA101, and EHA109.

Transformation is typically performed on a specific type of plant tissue. The present invention is compatible with any regenerable cotton tissues (i.e., tissue capable of forming a differentiated plant). Such tissue includes cell suspension, callus, meristem, hypocotyl, cotyledons, roots, floral tissue, petioles, anthers, leaves and immature embryos. In the practice of the present invention, the regenerable tissue is preferably hypocotyl or cotyledon tissue.

Preparation of *Agrobacterium* for inoculation of explants is generally well known to those of skill in the art. For purposes of the present invention, the *Agrobacterium* culture is initiated by inoculating a Petri plate containing a medium such as Luria-Bertani (LB) in agar with selective antibiotics. The concentration of selective agent as well as the particular selective agent utilized are variable and depend on the host strain. Those of skill in the art are also aware that the timing of culture growth, culture temperature, and concentration of host bacterium may be different for particular transformation systems. The inoculated plate may be incubated between about 23° C. and about 28° C., or about 26° C. and about 28° C., for several days. An individually isolated colony is used to inoculate an LB liquid culture containing selective antibiotics and grown to the proper concentration. The fresh liquid culture is sub-cultured again and then subsequently used for inoculation of the hypocotyl explants.

Preparation of hypocotyl explant tissue generated from cotton seeds is well known to those of skill in the art (e.g., U.S. Pat. No. 5,159,135). Briefly, cotton seeds are surface-sterilized and germinated in the dark or in a dark/light regime on appropriate media. In one embodiment, germination medium (Table 1 below) containing ½×MS salts with Gamborg's B5 vitamins and a sugar such as glucose or sucrose is used for germinating cotton seeds. Seeds typically germinate in about three to twelve days, and preferably in about three to eight days. Hypocotyl segments are removed from the seedlings. Hypocotyl segments are sectioned into small pieces between about 3 mm and about 10 mm in length. Care is taken to keep the hypocotyl hydrated from the time it is removed from its vessel until inoculation with *Agrobacterium* harboring a recombinant nucleic acid vector. In one embodiment, hypocotyl segments are incubated/pre-soaked in MSO glucose medium (Table 2 below). In another embodiment hypocotyl segments are incubated in the medium at room temperature for about 2 hrs. The incubation time at this step can vary from about 30 minutes to several hours e.g., eight hours prior to inoculation with *Agrobacterium* harboring a recombinant nucleic acid vector. The incubation/pre-soaking of hypocotyls in MSO glucose medium surprisingly resulted into reduced phenolics production at later stages of tissue culture and in better embryogenic response in terms of production of more callus in a shorter time (see Table 14). For inoculation, hypocotyl tissue or any other cotton tissue is treated with *Agrobacterium* suspension by soaking the explants in the *Agrobacterium* suspension for about 20 minutes. After the inoculation step, the excess *Agrobacterium* suspension is removed by blotting the explants on sterile filter paper.

The inoculated explants are then co-cultured with the *Agrobacterium* for one to five days, preferably one to three days at room temperature (i.e., about 22° C.-24° C.). The co-cultured tissue is subsequently transferred to a selective medium (Table 5 below) containing one or more antibiotics to prevent the growth of the *Agrobacterium*. The range of inhibitory antibiotics may vary, depending on the *Agrobacterium* strain used. Those of skill in the art are familiar with the antibiotics used to inhibit *Agrobacterium* remaining in the culture while allowing growth of the transgenic explant tissue. Examples of *Agrobacterium* inhibitory antibiotics useful for practice of this invention include carbenicillin and cefotaxime.

In addition to antibiotics to inhibit the growth of *Agrobacterium*, a selection agent is added to promote the growth of the transformed plant tissue. The selection agent is a substance that is toxic to non-transformed cotton cells but not to transformed cells. The transformed cells generally incorporate and produce a selectable marker protein at a level suitable to confer resistance to the selection agent. Selection agents used may generally be any selection agent compatible with the present invention. The selection agent may be kanamycin, for instance at a concentration between 15 mg/L and 150 mg/L, preferably between 40 mg/L and 70 mg/L. Alternatively, the selection agent may, for instance, be glyphosate at a concentration between 0.1 mM and 2.5 mM, for instance 2 mM in UMSEL or WPSEL medium and 0.1 mM in UMO medium, or glufosinate, for instance, at a concentration between 2.5 mg/L and 10 mg/L, e.g. about 5 mg/L. Other suitable selection agents may include an auxin-like herbicide such as dicamba, 2,4-D, or MCPA, an acetolactate synthase inhibitor, a protoporphyrinogen oxidase inhibitor, a hydroxyphenyl-pyruvate-dioxygenase inhibitor, neomycin, kanamycin, paramomycin, G418 or other aminoglycoside, spectinomycin, streptomycin, hygromycin B, bleomycin, phleomycin, sulfonamides, streptothricin, chloramphenicol, methotrexate, 2-deoxyglucose, betaine aldehyde, S-aminoethyl L-cysteine, 4-methyltryptophan, D-xylose, D-mannose, benzyladenine-N-3-glucuronidase. Genes that encode proteins that can detoxify these selection agents are well known to those skilled in the art. One skilled in the art will appreciate that the concentration of the selective agent may vary with the culture media employed, type of explant used, growth conditions, as well as the particular selective agent utilized.

Many different forms of media are suitable for the selection of transformed cells. One skilled in the art is familiar with the varieties of media that, when supplemented appropriately, support plant tissue growth and development. MS medium (Murashige and Skoog, 1962) Gamborg's medium (Gamborg et al., 1968), LM Woody Plant Medium (WPM) (McCown and Lloyd, 1981), Nitsch and Nitsch medium (Nitsch and Nitsch, 1969), and Schenk and Hildebrandt medium (Schenk and Hildebrandt, 1972). MS medium with supplements including vitamins such as $B_5$ (Gamborg), phytohormones such as 2,4-D and kinetin, and a carbohydrate source such as glucose may be used for regeneration of cotton plants.

According to the present disclosure, the term "sucrose pulse" refers to the transfer of a cotton explant or cell culture from a given growth medium to a similar growth medium, however additionally comprising sucrose, for a defined period of time during the callus formation phase of growth, i.e. non-embryogenic callus growth, followed by additional growth on the given medium. In certain embodiments the sucrose pulse is carried out for about 1 week on media comprising about 0.1 g/L sucrose. The given growth medium may comprise, for instance, MS basal salts, or LM woody plant medium basal salts.

In a particular embodiment, woody plant medium (WPM) basal salts were used instead of MS medium basal salts to prepare a modified WPM medium (Table 12) for selecting transformed callus.

The present disclosure envisions altering the cells' gaseous environment for cotton tissue culture. One of skill in the art may actively alter the gaseous environment of a cotton tissue culture by several means, for example by adding or taking out any material by physical or chemical means that can affect the composition of the air surrounding the culture. Tissue culture may be performed in an enclosed system such as a Petri plate, and/or in an incubator where other parameters including light and temperature may be controlled. In one embodiment of the invention, the chemical composition of the growth medium is formulated to enhance production of gases or other metabolites that may change the gas composition of the growth environment. An example of such a formulation would be the addition of an ethylene precursor in the growth medium, to produce higher concentration of ethylene in the growth environment, at an appropriate stage in the cell culture process.

In another embodiment, the air composition of growth environment may be altered by adding or removing gasses from the environment. Addition of ethylene or any desired gas can easily be done by flushing the incubator with the gas. Air composition of cotton tissue culture growth environment can also be altered by application of complete or partial vacuum in the incubator. Air composition of cotton tissue culture environment can also be accomplished by placement of chemicals, for example: the placement of a concentrated sodium hydroxide solution in the incubator can remove carbon dioxide from the culture's gaseous environment. A "low oxygen environment" refers to a plant cell culture growth environment in which $O_2$ content is less than that typically found in the atmosphere but is still suitable for normal growth and development. For instance, an atmosphere comprising from about 5 to 10% $O_2$, preferably about 9% $O_2$ is a low oxygen environment.

Thus, one embodiment of the present invention envisions placement of a chemical that can remove a gas from the culture's environment, in order to alter the composition of environment and to alter the culture's growth. In another embodiment of the invention, the air composition of a cotton tissue culture environment may be altered by sealing the tissue culture vessel in which cotton tissue culture is carried out. Sealing of cotton tissue culture vessel can be done, for instance, by use of a tape or membrane that can affect the culture's gas exchange. An example would be the sealing of a cotton tissue culture vessel with PARAFILM, SARAN wrap or another plastic film, turkey bags, zip lock bag and the like. As an example, the sea level composition of the major components of the atmosphere is given in Table 1 (Lide et al., 1997). According to the present disclosure, an altered atmospheric composition includes an air composition (i.e. a gaseous environment) wherein the ratio of the listed gases is actively changed from that of Table 1.

TABLE 1

The sea-level composition of air (in percent by volume at a temperature of 15° C. and a pressure of 101325 Pa).

| Name | Symbol | Percent by Volume |
|---|---|---|
| Nitrogen | $N_2$ | 78.08% |
| Oxygen | $O_2$ | 20.95% |
| Argon | Ar | 0.93% |
| Carbon Dioxide | $CO_2$ | 0.03% |
| Neon | Ne | 0.00% |
| Methane | $CH_4$ | 0.00% |
| Helium | He | 0.00% |
| Krypton | Kr | 0.00% |
| Hydrogen | $H_2$ | 0.00% |
| Xenon | Xe | 0.00% |

The timing of the alteration of the cotton cells' gaseous environment may also influence the effect of the environment on the culture, and its growth and embryogenesis. Thus, in one embodiment, ethylene, an ethylene precursor, or other agent that enhances ethylene levels, may be added to culture media or to the environment (e.g. flask, vessel, plate, incubator, room air flow, etc.) of a cotton cell culture during the callus induction phase of cell growth, for instance when cotton cells are placed in contact with a UMSEL, WPSEL or UMSEL- or WPSEL-like medium, for instance following a "sucrose pulse" step, however with the proviso that the ethylene enhancement is discontinued when the induction-of-embryogenesis step commences.

Those of skill in the art are aware of other important variables that may be altered in the tissue culture conditions. Temperature is one such other variable. Cotton cell transformation and regeneration processes are generally performed in a temperature range between about 20° C. and about 30° C., and 20° C. to 28° C. is a typical temperature range for cotton callus induction and regeneration of a cotton plant. Similarly, induction of cotton embryogenesis, embryo maturation, and embryo germination are usually performed at a temperature of about 20° C. to 28° C. The present invention contemplates, in certain embodiments, a temperature of >28° C. for cotton callus induction, induction of cotton embryogenesis, embryo maturation, and embryo germination. Growth of treated cotton cells and tissues in elevated temperature may be combined with one or more other described treatment(s) to yield additional or synergistic improvements in the level and timing of formation of embryogenic callus, germinable embryos, and resulting cotton plants. In a particular embodiment one or more of these steps for cotton may be carried out at a temperature from more than about 30° C. to about 35° C.

Cotton plant tissue is often cultured with a 16-hour day and 8-hour night photoperiod with light intensities between about 20 µEinsteins $m^{-2}$ $s^{-1}$ and about 200 µEinsteins $m^{-2}$ $s^{-1}$, unless other conditions are specified. During the phases of cotton cell culture, including seed germination, callus formation, the embryogenic callus induction phase, and the embryo proliferation stage, the cotton tissue may be maintained in the dark in order to promote embryogenesis, embryo formation or maturation (e.g on UMSEL, WPSEL, or UMO medium). In one embodiment, a cotton seed may be germinated and then grown under dark lighting conditions of 0 µEinsteins $m^{-2}$ $sec^-$, to obtain a cotton seedling comprising a hypocotyl. The hypocotyl may be excised from the germinated seedling to obtain a hypocotyl explant that may then be grown further or transformed prior to further growth.

In some embodiments, the seed may be germinated, and grown under dark lighting conditions of 0 µEinsteins $m^{-2}$ $sec^{-1}$ for 2-4 days, such as for 3 days, before being placed in the light for a further 12-24 hours prior to using the germinated seed for callus induction, and subsequent culture under the described conditions that lead to formation of embryogenic callus. In certain embodiments, the callus formation medium comprises MS basal salts, such as found in UMSEL medium. In other embodiments the callus formation medium comprises modified basal salts, such as found in WPSEL medium, or similar. The explant may also be soaked in a liquid culture medium, such as MSO with glucose, prior to undergoing transformation (e.g. co-cultivation with an *Agrobacterium* culture comprising a gene of interest).

Transformed tissue may be maintained on the selection medium, or an equivalent medium, for about two to ten weeks, preferably about four to nine weeks. Transfers are performed as needed, generally every three to five weeks. The callus tissue may be removed from the hypocotyl pieces and transferred to a medium suitable for the induction of embryogenic callus tissue. As stated above, multiple compositions of media are applicable to plant transformation and regeneration. The present invention may use UMO for the embryogenic callus induction step.

The media described herein may comprise a gelling agent such as Gelrite® or Gelzan™ (Gelzan is a trademark of CP Kelco U.S., Inc., Houston, Tex.; GELRITE is registered trademark of CP Kelco), or PHYTAGEL (PHYTAGEL is a registered trademark of Sigma Chemical Co., St. Louis, Mo.). The gelling agent is typically added at a concentration between about 2 g/L and about 3.5 g/L. The callus induction medium typically contains a carbohydrate. For instance, glucose or maltose may be employed as a carbon source. The plates may be incubated at about 30° C. with an approximate 16/8 hour day/night cycle. Light intensity may range, for instance, from about 20 µEinsteins $m^{-2}$ $s^{-1}$ to about 100 µEinsteins $m^{-2}$ $s^{-1}$.

The embryogenic callus induction medium may contain an antioxidant to promote the process of embryogenesis. A combination of antioxidants was found to decrease tissue necrosis in grape-*Agrobacterium* interactions (Perl et al., 1996). Those of skill in the art are familiar with the broad range of antioxidants available.

Approximately every eight weeks, for instance every six to eight weeks, actively growing tissue and small embryos are removed and placed on Petri plates containing fresh semi-solid medium with a support matrix as described (for instance semi-solid medium that is overlaid by a sterile Whatman filter) for an additional eight to twelve weeks. This embryogenic tissue may be sub-cultured to the same medium every 4-6 weeks. The plates may be cultured at about 28-30° C. in darkness.

Embryos larger than about 5 mm are individually transferred to an embryo germination medium. This medium is for instance Stewart and Hsu (SHSU) medium (Stewart and Hsu, 1977). The germination medium typically contains glucose as a carbohydrate at a concentration between about 1.0% (w/v) and about 10.0% (w/v), and more preferably about 5.0% (w/v). Other carbohydrates, such as maltose are also envisioned to have similar utility at low concentrations, and fall within the scope of the present invention. Incubation in the germination medium with an approximate 16/8 hour day/night cycle may, for instance, be carried out from about two to eight weeks, and often from about three to about four weeks.

The embryos are routinely monitored for germination. Embryos that have formed 2-3 leaves are generally transferred to a larger culture container and cultured further in the germination medium. The germinated embryos, or plantlets, are maintained in culture at about 28-30° C. with an approximate 16/8 hour day/night cycle, and typically with a light intensity of about 50-300 µEinsteins $m^{-2}$ $s^{-1}$.

When plantlets have a total of four to six true leaves, and a well-established root system, the plantlets are transplanted to soil, grown in a growth chamber, and subsequently transferred to a greenhouse. In one embodiment, MetroMix 350 (Hummerts Inc., St. Louis, Mo.) which has been supplemented with a slow release fertilizer is used. A variety of soil mixtures are available and may be used in the practice of this invention. Plants may be grown at about 28° C. with a 16/8 hour day/night cycle to obtain mature reproductive cotton plants.

A transgenic plant formed using *Agrobacterium* transformation methods typically contains a single simple recombinant DNA sequence inserted into one chromosome and is referred to as a transgenic event. Such transgenic plants can be referred to as being heterozygous for the inserted exogenous sequence. A transgenic plant homozygous with respect to a transgene can be obtained by sexually mating an independent transgenic plant that contains a single exogenous gene sequence, for example an $R_0$ plant, to produce $R_1$ seed. If the $R_0$ plant is selfed, one fourth of the $R_1$ seed produced will be homozygous positive with respect to the transgene. Germinating $R_1$ seed results in plants that can be tested for zygosity, typically using a SNP assay or a thermal amplification assay that allows for the distinction between heterozygotes and homozygotes (i.e., a zygosity assay) or other assays known to those skilled in the art.

To confirm the presence of the exogenous DNA or "transgene(s)" in the transgenic plants a variety of assays may be performed. Such assays include, for example, "molecular biological" assays, such as Southern and northern blotting and PCR™, INVADER assays; "biochemical" assays, such as detecting the presence of a protein product, e.g., by immunological means (ELISAs and western blots) or by enzymatic function; plant part assays, such as leaf or root assays; and also, by analyzing the phenotype of the whole regenerated plant.

Once a transgene has been introduced into a plant, that gene can be introduced into any plant sexually compatible with the first plant by crossing, without the need for ever directly transforming the second plant. Therefore, as used herein the term "progeny" denotes the offspring of any generation of a parent plant prepared in accordance with the instant invention, wherein the progeny comprises a selected DNA construct. A "transgenic plant" may thus be of any generation. "Crossing" a plant to provide a plant line having one or more added transgenes or alleles relative to a starting plant line is defined as the techniques that result in a particular sequence being introduced into a plant line by crossing a starting line with a donor plant line that comprises a transgene or allele. To achieve this one could, for example, perform the following steps: (a) plant seeds of the first (starting line) and second (donor plant line that comprises a desired transgene or allele) parent plants; (b) grow the seeds of the first and second parent plants into plants that bear flowers; (c) pollinate a flower from the first parent plant with pollen from the second parent plant; and (d) harvest seeds produced on the parent plant bearing the fertilized flower.

The present invention also provides for plant parts or a plant produced by the methods of the present invention. Plant parts, without limitation, include fruit, seed, endosperm, ovule, pollen, leaf, stem, and roots. In a preferred embodiment of the present invention, the plant part is a seed.

EXAMPLES

The following examples are included to demonstrate embodiments of the invention. However, those of skill in the art should, in light of the present disclosure, appreciate that many changes and substitutions can be made in the specific embodiments that are disclosed and still obtain a like or similar result without departing from the spirit and scope of the invention.

Example 1

Seed Sterilization, Germination, and Tissue Preparation

Cotton seeds (cv. Coker 130) were stored at 4° C. at or below 30% humidity, in the dark for long-term viability. The seeds were removed from 4° C. storage and were added to a one-liter disposable bottle. About ¼ teaspoons of a phosphate free detergent such as LABTONE detergent (VWR International, West Chester, Pa.) with about 800 mL of sterile water was added to the bottle. The bottle was capped and the seeds shaken and allowed to soak for 10 minutes. The bottle was occasionally swirled during the soaking process to wash the seeds thoroughly. The seeds were then rinsed, with sterile water, to help remove any remaining foam from the detergent. After draining all the water approximately 200 ml of 70% ethanol was added to cover all the seeds in the bottle followed by gentle swirl for 2-3 minutes. Ethanol was drained and seeds were washed again with sterile water. Approximately 800 ml of 50% bleach solution, 3 drops of TWEEN 20 (EMD BIOSCIENCES, San Diego, Calif.) with a laboratory magnetic bar was added to the bottle with the seeds and seeds were gently stirred at a low speed on a magnetic stir plate for about 30 minutes. After 30 minutes, solution from bottle was drained and seeds were washed 2-4 times with sterile deionized water. Seeds were germinated in the dark or light-limiting conditions on germination medium (Table 2) in a tall tissue culture vessel such as a PHYTATRAY (PHYTATRAY is a registered trademark of Sigma Chemical Co., St. Louis, Mo.) for about five to ten days. The hypocotyl segments were removed from the dark or limited-light grown seedlings and sectioned into small pieces. These sections of hypocotyl segments were incubated in liquid MSO glucose medium (Table 3) at room temperature for 1-3 hrs prior to inoculation.

TABLE 2

Composition of seed germination medium.

| Component | Amount/L |
|---|---|
| MS basal salts (Phytotech) | 2.5 g |
| Gamborg's B5 vitamins (Phytotech) (500X) | 2 ml |
| Glucose | 10 g |
| pH | 5.8 |

TABLE 3

Composition of MSO Glucose medium.

| Component | Amount/L |
|---|---|
| MS basal salts (Phytotech.) | 4.33 g |
| Gamborg's B5 vitamins (Phytotech) (500X) | 2 ml |
| Glucose | 30 g |
| pH | 5.7 |

Example 2

Preparation of *Agrobacterium* Cells for Inoculation of Cotton Hypocotyl Segments Prepared in Example 1

*Agrobacterium* strain C58 was streaked from a glycerol stock onto a Luria Broth plate (10 g/L sodium chloride, 5 g/L yeast extract, 10 g/L bacto-tryptone solidified with 15 g/L agar on a Petri plate, referred to as "LB plate") containing the following selective antibiotics per liter: spectinomycin (1 mL of a 50 mg/mL stock), streptomycin (1 mL of a 50 mg/mL stock), chloramphenicol (1 mL of a 25 mg/mL stock), and kanamycin (1 mL of a 50 mg/mL stock). The plate was incubated at about 28° C. for about 3 days. From one to three colonies were used to inoculate 2 mL of liquid culture of LB containing selective antibiotics described above. This liquid culture was allowed to grow approximately 20 hours at 28° C. on a rotary shaker to make an active liquid culture of the bacteria. Two mL of active liquid culture was used to inoculate 20 mL of liquid LB medium with selective antibiotics and allowed to grow approximately 20 hours at 28° C. on a rotary shaker. The bacterial culture was centrifuged, washed and resuspended in MSO medium (Table 4), which is similar to the medium of Table 3 except for the carbohydrate source. Optical density ($OD_{660}$) of resuspended bacterial cells in MSO medium was measured and adjusted to about 0.1 to 1.0.

TABLE 4

Composition of MSO medium.

| Component | Amount/L |
|---|---|
| MS basal salts (Phytotech) | 4.33 g |
| Gamborg's B5 vitamins (Phytotech) (500X) | 2 ml |
| Sucrose | 30 g |
| pH | 5.7 |

Example 3

Inoculation of Cotton Hypocotyl Segments with *Agrobacterium*

Hypocotyl segments or explants were placed on a sterile Petri plate under aseptic conditions and covered with sufficient bacterial suspension. The Petri plate was covered and swirled frequently for about 20 minutes to ensure good contact of bacterial suspension with explants. After 20 minutes bacterial suspension was aspirated from the plate and explants were blotted with sterile filter paper to remove excess suspension under aseptic conditions. These explants were placed as a single layer on co-culture plate with TrCO medium (Table 5). Plates were covered with plastic bag, cultured in a covered box and incubated at 22-24° C. with 10 hour light/14 hour dark photoperiod for about 2 to 3 days.

TABLE 5

Composition of TrCO Medium

| Component | Amount/L |
|---|---|
| MS basal salts (Phytotech) | 0.433 g |
| Gamborg's B5 vitamins (Phytotech) (500X) | 2 ml |
| 2,4-D (1 mg/ml) | 0.1 ml |
| Kinetin (0.5 mg/ml) | 0.2 ml |
| Glucose | 30 g |
| pH | 5.8 |
| Agar (Sigma) | 9 g |

Example 4

Selection of Transformed Cells and Production of Cotton Non-Embryogenic Callus

Two to three days after inoculation (and treatment of explants as described in above example); hypocotyl explants were transferred to a Petri plate with UMSEL containing appropriate selection agent (Table 6). Petri plate was sealed with Parafilm and incubated at 28° C. with a 16/8 (day/night) cycle for about 4 weeks. After 4 weeks hypocotyls were transferred to a sucrose pulse medium (e.g. containing components as listed in Table 7). Hypocotyls were incubated for about another week in the sucrose pulse medium after sealing plates with PARAFILM at 28° C. with a 16/8 (day/night) cycle after which hypocotyl pieces were incubated in UMSEL medium (Table 6), under the same conditions as mentioned above, for another 4 weeks. After 4 weeks, clumps of callus were separated from hypocotyl end and placed on Petri plates with UMO medium (Table 7). Plates were sealed with PARAFILM and incubated at 28° C. in darkness to generate embryogenic callus.

TABLE 6

Composition of UMSEL selection medium.

| Component | Amount/L |
|---|---|
| MS basal salts (Phytotech) | 4.33 g |
| Gamborg's B5 vitamins (Phytotech) (500X) | 2 ml |
| 2,4-D (1 mg/ml) | 0.1 ml |
| Kinetin (0.5 mg/ml) | 1 ml |
| Glucose | 30 g |
| pH | 5.8 |
| Phytagel (Sigma) | 2.5 g |
| Carbenicillin (250 mg/ml) | 1.7 ml |
| Cefotaxime (100 mg/ml) | 1 ml |
| Kanamycin (50 mg/ml) | 0.9 ml |

TABLE 7

Composition of Sucrose Pulse medium.

| Component | Amount/L |
|---|---|
| MS basal salts (Phytotech) | 4.33 g |
| Gamborg's B5 vitamins (Phytotech) (500X) | 2 ml |
| 2,4-D (1 mg/ml) | 0.1 ml |
| Kinetin (0.5 mg/ml) | 1 ml |
| Glucose | 30 g |
| pH | 5.8 |
| Phytagel (Sigma) | 2.5 g |
| Carbenicillin (250 mg/ml) | 1.7 ml |
| Cefotaxime (100 mg/ml) | 1 ml |
| Kanamycin (40-50 mg/ml) | 0.9 ml to 1.0 ml |
| Sucrose | 0.1 g |

Example 5

Generation of Embryogenic Callus and Embryo Maturation from Non-Embryogenic Callus Callus from above example was incubated for 6-8 weeks at 28° C. in the dark. After 6-8 weeks depending on growth rate callus was separated into several clumps. Two calli from each of the clumps were placed on fresh UMO plates (Table 8) and sealed with PARAFILM. These plates were again incubated for 8-10 weeks at 28° C. in dark. After about 6 weeks to about 10 weeks, plates were checked for generation of embryogenic callus characterized by discrete units of friable or compact calli clumps and/or various maturation stages of somatic embryos. The embryogenic callus and somatic embryos are readily identified by their morphological appearance and are often distinguished by their feel when they are probed with forceps. Non-embryogenic callus, in contrast, is softer at this stage without organized discrete calli clumps.

TABLE 8

Composition of UMO selection medium.

| Component | Amount/L |
|---|---|
| MS basal salts (Phytotech) | 4.33 g |
| Gamborg's B5 vitamins (Phytotech) (500X) | 2 ml |
| Glucose | 30 g |
| pH | 5.8 |
| Gelrite (Kelco) | 3.5 g |
| Carbenicillin (250 mg/ml) | 1.7 ml |
| Cefotaxime (100 mg/ml) | 1 ml |
| Kanamycin (50 mg/ml) | 1 ml |
| Ascorbic acid | 100 mg |

Embryogenic callus with embryos from above was placed on TRP+ medium (Table 9) for maturing embryos and incubated as described above. Every 3-5 weeks, for approximately 3 months, actively growing tissue and small embryos were transferred to fresh TRP+ medium plates until embryos attained a size of approximately 5 millimeters.

TABLE 9

Composition of TRP+ medium.

| Component | Amount/L |
|---|---|
| MS basal salts (Phytotech) | 4.33 g |
| Gamborg's B5 vitamins (Phytotech) (500X) | 2 ml |
| Glucose | 30 g |
| Potassium nitrate | 1.9 g |
| Casein hydrolysate | 0.1 g |
| pH | 5.8 |
| Gelrite (Kelco) | 3.5 g |
| Carbenicillin (250 mg/ml) | 1.7 ml |
| Cefotaxime (100 mg/ml) | 1 ml |
| Benlate (50 mg/ml) | 1 ml |

Five millimeter or larger embryos were carefully removed and transferred to fresh plates with SHSU medium (Table 10) under aseptic conditions. Old plates with TRP+ medium were resealed and placed back for incubation and generation of more mature embryos. New plates with SHSU medium were also sealed with PARAFILM to incubate at 28° C. with 16/8 (day/night) cycle with maximum lighting up to 100 µEinsteins $m^{-2}$ $s^{-1}$. Every 4-6 weeks, shoots on these plates were checked for growth and development. Each shoot with 3-4 leaves and a developed root system was transferred to a sundae cup with fresh SHSU medium and further incubated at 30° C. with 16/8 (day/night) cycle. Shoots were incubated until they reached the 4-5 leaf stage and abundant new root growth was observed. Shoots with 4-5 leaves and a mature root system were transferred to pots with soil to obtain a mature cotton plant.

TABLE 10

Composition of SHSU medium.

| Component | Amount/L |
| --- | --- |
| Stewart and Hsu majors (10X) | 100 ml |
| Stewart and Hsu minors (100X) | 10 ml |
| Steward and Hsu organics (100X) | 10 ml |
| Chelated iron (100X) | 1.5 ml |
| Glucose | 5 g |
| pH | 6.8 |
| Gelrite (Kelco) | 2.2 g |
| Benlate (50 mg/ml) | 1 ml |

Example 6

Effect of Brassinosteroid on Enhancing Cotton Embryo Formation

A brassinosteroid plant growth regulator was used to enhance cotton embryo formation. Brassinolide (i.e. 24-epi-brassinolide; Super-Grow, Montreal, Calif.), at a concentration from 2 to 100 μM was added to TRP+ medium (Table 9). Embryogenic callus from the UMO medium (Table 8) was then cultured on TRP+ medium containing Brassinolide. A substantial increase in the number of embryos produced was seen in the cultures grown with brassinolide treatment, compared to the untreated control, with 5 to 10 μM brassinolide being optimal in this experiment. Besides an increase in the overall production of embryos, many of the embryos produced from the brassinolide treatment were 5-6 mm long heart shaped embryos (more developed), whereas there were none at this stage in the control treatment. These results clearly demonstrate that brassinolide or another brassinosteroid may be utilized to increase the likelihood of cotton embryo development and growth from embryogenic callus, as well as the degree of the development. Results are shown on Table 11.

TABLE 11

The effect of brassinolide treatment on the production of embryos from embryogenic cotton callus.

| | | Embryo stages | |
| --- | --- | --- | --- |
| Treatment | Total embryos | 2-3 mm globules | 5-6 mm heart shaped |
| 2 μM Brassinolide | 3 | 3 | 0 |
| 5 μM Brassinolide | 18 | 10 | 8 |
| 10 μM Brassinolide | 17 | 6 | 11 |
| 15 μM Brassinolide | 15 | 6 | 9 |
| Control with Ethanol | 3 | 3 | 0 |

Example 7

Effect of Brassinolide, Low Oxygen Supply, and a Combination of Both on Enhancing Cotton Embryo Maturation Brassinolide was observed to enhance cotton embryo formation in the presence of oxygen ($O_2$). When embryogenic callus was placed on brassinolide containing TRP+ medium (Table 9) at either 9% or 21% $O_2$, more embryos were produced in the brassinolide treatments at 9% than at 21% $O_2$. Lower level of 10 μM brassinolide gave the greatest response at 9% $O_2$ but 100 μM level of brassinolide was more useful in 21% $O_2$. Lower level of $O_2$ was observed to be beneficial in producing more embryos than higher level of $O_2$ (Table 12). Different levels of $O_2$ were created by using a PRO-OX 110 oxygen control according to manufacturer's instructions (BioSpherix, Redfield, N.Y.) in a growth chamber (e.g. Percival Scientific, Inc., Perry, Iowa). Results in Table 12 indicate that brassinolide promotes the growth and development of embryos from cotton embryogenic callus.

TABLE 12

The effect of brassinolide on embryo production at 9% and 21% $O_2$ levels.

| | Number of Embryos Produced | | | | | |
| --- | --- | --- | --- | --- | --- | --- |
| | 21% $O_2$ | | | 9% $O_2$ | | |
| Treatment | 4 weeks | 7 weeks | 9 weeks | 4 weeks | 7 weeks | 9 weeks |
| Control with Ethanol | 18 | 13 | 15 | 1 | 5 | 22 |
| 10 μM Brassinolide | 21 | 28 | 21 | 18 | 30 | 48 |
| 50 μM Brassinolide | 10 | 8 | 11 | 8 | 12 | 35 |
| 100 μM Brassinolide | 6 | 9 | 33 | 1 | 9 | 21 |

Example 8

Method for Accelerating Induction of Embryogenic Cotton Callus by Using LM Woody Plant Medium (WPM) Basal Salt Mixture and Other Media Supplements During Callus Induction Step In the medium, WPM basal salt mixture was used in place of MS basal salt mixture during the callus induction step. The new modified medium is referred as WPSEL medium (Table 13). As shown in Table 15 (in treatment 10) WPSEL promoted early somatic embryogenesis of cotton when used during the callus induction step.

In addition to testing a modified basal salt mixture such as found in Woody Plant Medium, the effect of pre-soaking hypocotyl explants in liquid MSO glucose medium (Table 3), and callus induction at different temperature was also tested. After 2 hr of pre-soaking, the explants were placed on either UMSEL (Table 6) or WPSEL (Table 13) medium. The plates were unwrapped at this step except for treatment 9 (Table 15) and cultured at specified temperature for callus induction. Calli produced at the end of 4 week period were transferred to UMO medium for embryogenic callus induction. Half of the plates were wrapped, and the other half were unwrapped for each treatment.

TABLE 13

Composition of WPSEL Medium.

| Component | Amount/L |
| --- | --- |
| LM Woody Plant Basal Salts (Phytotech). | 2.3 g |
| Gamborg's B5 vitamins (Phytotech) (500X) | 2 ml |
| 2,4-D (1 mg/ml) | 0.1 ml |
| Kinetin (0.5 mg/ml) | 1 ml |

TABLE 13-continued

Composition of WPSEL Medium.

| Component | Amount/L |
|---|---|
| Glucose | 30 g |
| Phytagel (Sigma) | 2.5 g |
| Carbenicillin (Phytotech) | 425 mg |
| Cefotaxime (Midwest) | 100 mg |
| pH | 5.8 |

TABLE 14

Composition of Inoculation Medium.

| Components | Amount/L |
|---|---|
| MS Basal Salts (Phytotech) | 2.165 g |
| MS Vitamins (100 x) (Phytotech) | 10 ml |
| Sucrose (Phytotech) | 68.5 g |
| Glucose (Phytotech) | 36 g |
| Proline (Fisher) | 0.115 g |
| pH | 5.4 |

The results shown in Table 15 demonstrate that WPM salts in combination with pre-soaking of the explant in MSO medium and culturing at 30° C. with the plates wrapped (Treatment 6) significantly improved embryogenic callus induction. This method not only showed higher frequency of embryogenic callus induction earlier (Treatments 2, 4, 6, 8, 10), but produced much larger masses of embryogenic callus than its MS salts-based medium counterparts (Treatments 1, 3, 5, 7, 9).

Further, when media supplements such as abscisic acid (0.03, 0.15, 0.75 mg/L) were added to the WPSEL medium, production of embryogenic callus improved further as shown in Table 16.

Additionally, Table 17 compares the effect of seedling growth conditions on embryogenic callus (EC) production. Hypocotyls that were grown in dark and cultured on WPSEL produced more embryogenic callus faster. Hypocotyls and cotyledons that were taken from seedlings that were first grown in dark and then in light also produced more embryogenic callus faster. It was also surprising to see that hypocotyls which were taken from seedlings that were first grown in dark and then in light produced more embryogenic callus even on UMSEL medium as opposed to hypocotyls that were grown in dark only indicating that manipulation of lighting condition for seedling growth in itself has beneficial effect on production of embryogenic callus.

TABLE 15

Effect of different basal salts, pre-soaking the explant, and temperature at callus induction step, on embryogenic callus production. % EC (embryogenic callus) formation is expressed as the number of callus showing embryogenic callus formation (regardless of the size of the embryogenic callus) divided by the total number of explants × 100.

| Treatment | 2 hr Pre-soaking | Soaking Medium | Callus Induction Temp. (° C.) | Callus Induction Medium | % EC Formation on UMO at 4 wk | % EC Formation on UMO at 6 wk | |
|---|---|---|---|---|---|---|---|
| | | | | | | Plates wrapped | Plates unwrapped |
| 1 | Yes | Inoculation | 30 | UMSEL | 0 | 0 | 0 |
| 2 | | Medium | | WPSEL | 27.8 | 44.4 | 27.8 |
| 3 | | (Table 14) | 28 | UMSEL | 0 | 0 | 0 |
| 4 | | | | WPSEL | 22.2 | 38.9 | 38.9 |
| 5 | | MSO | 30 | UMSEL | 5.6 | 5.6 | 11.1 |
| 6 | | glucose | | WPSEL | 44.4 | 82.4 | 50 |
| 7 | | Medium | 28 | UMSEL | 0 | 0 | 0 |
| 8 | | | | WPSEL | 27.8 | 50 | 27.8 |
| 9 | No | N/A | 28 | UMSEL | 0 | 11.1 | 5.6 |
| 10 | | | | WPSEL | 27.8 | 55.6 | 44.4 |

TABLE 16

Effect of abscisic acid in combination with WPSEL, on embryogenic callus production.

| Explant | Treatment | Total # pieces | 7.5 weeks on UMO | | 10 weeks on UMO | |
|---|---|---|---|---|---|---|
| | | | # Pieces with EC | % EC | # Pieces with EC | % EC |
| Hypocotyl | UMSEL (control) | 32 | 0 | 0.0 | 11 | 34.4 |
| | WPSEL | 32 | 16 | 50.0 | 29 | 90.6 |
| | WPSEL + ABA 0.03 mg/L | 32 | 21 | 65.6 | 29 | 90.6 |
| | WPSEL + ABA 0.15 mg/L | 32 | 24 | 75 | 32 | 100.0 |
| | WPSEL + ABA 0.75 mg/L | 32 | 28 | 87.5 | 32 | 100.0 |
| Cotyledon | UMSEL (control) | 32 | 0 | 0.0 | 0 | 0.0 |
| | WPSEL | 28 | 3 | 10.7 | 14 | 50.0 |
| | WPSEL + ABA 0.03 mg/L | 32 | 3 | 9.4 | 6 | 18.8 |
| | WPSEL + ABA 0.15 mg/L | 32 | 2 | 6.3 | 9 | 28.1 |
| | WPSEL + ABA 0.75 mg/L | 32 | 4 | 12.5 | 7 | 21.9 |

% EC (embryogenic callus) is expressed as the number of callus showing embryogenic callus formation (regardless of the size of the embryogenic callus) divided by the total number of explants × 100.

TABLE 17

Effect of seedling growth conditions on embryogenic callus (EC) production.

| Seedling growth conditions | Explant | Callus Medium Treatment | Total # pieces | # Pieces with EC |
|---|---|---|---|---|
| Dark | hypocotyl | UMSEL | 50 | 3 |
|  |  | WPSEL | 25 | 8 |
| Dark-Light | hypocotyl | UMSEL | 50 | 18 |
|  |  | WPSEL | 25 | 14 |
| Dark-Light | cotyledon | UMSEL | 50 | 1 |
|  |  | WPSEL | 50 | 5 |

% EC (embryogenic callus) is expressed as the number of callus showing embryogenic callus formation (regardless of the size of the embryogenic callus) divided by the total number of explants × 100.
Dark: seeds were germinated in dark for 4 days;
Dark-Light: seeds were germinated in dark for 3 days and 1 day in light (e.g. about 30 μE, 16/8 day night).

Differences between MS and LM Woody Plant basal salt compositions are shown in Table 18. Another medium having similar composition and concentration of individual components to LM Woody Plant medium basal salts would also be suitable for practicing this invention. Those skilled in the art would now be able to manipulate individual components of WPM and utilize those components that are useful for accelerating cotton embryogenic callus induction.

TABLE 18

Comparison of MS basal and WPSEL basal salt compositions.

| Components (mg/L) | MS salts | WPM salts |
|---|---|---|
| Ammonium nitrate | 1650 | 400 |
| Boric acid | 6.2 | 6.2 |
| Calcium chloride, anhydrous | 332.2 | 72.5 |
| Calcium nitrate | — | 386 |
| Cobalt chloride•$6H_2O$ | 0.025 | — |
| Cupric sulfate•$5H_2O$ | 0.025 | 0.25 |
| $Na_2$ EDTA | 37.26 | 37.3 |
| Ferrous sulfate•$7H_2O$ | 27.8 | 27.85 |
| Magnesium sulfate | 180.7 | 180.7 |
| Manganese sulfate•$H_2O$ | 16.9 | 22.3 |
| Molybdic acid (Na salt)•$2H_2O$ | 0.25 | 0.25 |
| Potassium iodide | 0.83 | — |
| Potassium nitrate | 1900 | — |
| Potassium phosphate, monobasic | 170 | 170 |
| Potassium sulfate | — | 990 |
| Zinc sulfate•$7H_2O$ | 8.6 | 8.6 |

Example 9

Method for Accelerating Induction of Embryogenic Callus in Cotton by Application of an Ethylene Precursor An ethylene precursor, 1-aminocyclopropane-1-carboxylic acid (ACC) was added at the step of undifferentiated callus formation, and removed prior to embryogenesis, to speed up embryogenic callus formation.

Three studies were performed to define the effect of ACC on enhancing embryogenic callus formation. In the first experiment summarized in Table 19, hypocotyl explants were placed on UMSEL medium containing different concentrations of ACC (Treatments 2-6), or containing no ACC (treatment 7). The plates were unwrapped and placed in two separate boxes (Treatments 2-6 in one box and Treatments 7-12 in another), and cultured at 28° C. with a photoperiod of 16 hr light/8 hr darkness. After four weeks of callus induction, the calli were transferred to UMO medium without ACC (Treatments 2-6), or to UMO plus different concentrations of ACC (Treatments 8-12) for embryogenic callus induction. The plates were wrapped with PARAFILM at this stage.

As shown in Table 19, addition of ACC during embryogenic callus induction, but not during callus induction had little positive effect, and in some cases reduced embryogenic callus induction (Treatments 8-12), whereas addition of ACC during callus induction, and its subsequent removal prior to induction of embryogenesis, dramatically promoted early embryogenic callus formation (Treatments 2-6, Table 19). At 7 weeks and 9 weeks after transferring to UMO medium for embryogenic callus induction, 80% and >90% of starting material produced embryogenic callus, respectively, when 10 μM of ACC was included in the medium during callus growth prior to embryogenic induction, compared to only 10% and 20% of the control. A range of ACC concentration of about 0.01 mM to about 1 mM yielded improved formation of embryogenic callus as compared to the control (no ACC).

TABLE 19

Effect of 1-aminocyclopropane-1-carboxylic acid (ACC) during callus induction or embryogenic callus induction step.

| Treatment | ACC (mM) | Total # explants | % EC at 7 week* | % EC at 9 week* |
|---|---|---|---|---|
| ACC at callus induction step (UMSEL) | | | | |
| 2 | 0.01 | 50 | 80 | 94 |
| 3 | 0.1 | 50 | 50 | 90 |
| 4 | 0.5 | 50 | 58 | 88 |
| 5 | 1 | 50 | 28 | 62 |
| 6 | 5 | 40 | 0 | 0 |
| 7 | 0 | 40 | 10 | 20 |
| ACC at embryogenic callus induction step (UMO) | | | | |
| 7 | 0 | 40 | 10 | 20 |
| 8 | 0.01 | 40 | — | 35 |
| 9 | 0.1 | 40 | — | 5 |
| 10 | 0.5 | 40 | — | 10 |
| 11 | 1 | 40 | — | 10 |
| 12 | 3 | 40 | — | 0 |

% EC (embryogenic callus) is expressed as the number of callus showing embryogenic callus formation (regardless of the size of the embryogenic callus) divided by the total number of explants × 100

Addition of ACC produced a similar enhancing effect on producing embryogenic callus from transformed tissue. The hypocotyl explants were inoculated with *Agrobacterium* containing a plant transformation vector pMON15722 having an expression unit conferring kanamycin tolerance. The explants were pre-soaked in 2-hr in MSO glucose medium (Table 3) before inoculation. After 2 days of co-culture at about 24° C., the inoculated hypocotyl pieces were placed on WPSEL medium containing 45 mg/L of kanamycin for 4 weeks for callus induction. After callus induction, the explants were again transferred to WPSEL medium for another 4 weeks. Different concentrations of ACC were incorporated in the medium at this step. The experimental design is presented in Table 20. In another experiment, the number of 5 mm embryos that were produced from calli was 22%, 19% (WPSEL+ACC) and 17%, 15% (WPSEL) indicating that the higher number of embryos can be produced by including ACC in the selection medium.

Other ethylene synthesis precursor or ethylene-releasing compounds known in the art, such as Ethephon (2-chloroethylphosphonic acid) may also be employed instead of, or in addition to, ACC.

TABLE 20

| Treatment | ACC conc. (µM) during non-embryogenic callus growth | % Pieces w/ EC after 6 weeks on UMO medium with Kanamycin |
|---|---|---|
| 1 | 0 | 16.8 |
| 2 | 10 | 18.4 |
| 3 | 30 | 22.1 |
| 4 | 60 | 21.6 |
| 5 | 100 | 26.5 |
| 6 | 150 | 44.0 |

Example 10

Enhanced Production of Transgenic Cotton Plants by Using Woody Plant Medium (WPM) Basal Salt Mixture During Callus Induction Step The hypocotyl explants were inoculated with *Agrobacterium* containing a plant transformation vector having a gene expression unit conferring kanamycin tolerance. The explants were then co-cultured and then placed on WPSEL medium containing 45 mg/L of kanamycin for callus induction and then successively transferred to the UMO medium, TRP+ medium, SHSU medium, and then to soil for regenerating transformed cotton plants. Table 21 shows that in 7 different experiments with 3 different gene of interest provided in plant transformation vectors comprising a kanamycin resistance expression unit, hypocotyl explants that were cultured on WPSEL consistently produced higher number of embryogenic calli giving rise to higher number of shoots and 1-2 copy events preferred for product development. The copy number was determined by Invader® assay (Third Wave™ Technologies, Madison, Wis.). This example confirmed the data obtained in Example 8 that the use of WPM salts at the non-embryogenic callus induction step enhances production of embryogenic callus and embryos at later steps.

TABLE 21

Production of transgenic cotton plants using WPM basal salt mixture.

| Experiment | Treatment | Calli | EC Calli | Selected Shoots in Soil |
|---|---|---|---|---|
| 1 | UMSEL | 794 | 105 | 2 |
|   | WPSEL | 1791 | 453 | 77 |
| 2 | UMSEL | 972 | 123 | 4 |
|   | WPSEL | 1850 | 607 | 89 |
| 3 | UMSEL | 1050 | 307 | 19 |
|   | WPSEL | 1610 | 676 | 38 |
| 4 | UMSEL | 1532 | 462 | 5 |
|   | WPSEL | 1594 | 730 | 13 |
| 5 | UMSEL | 720 | 183 | 4 |
|   | WPSEL | 923 | 334 | 12 |
| 6 | UMSEL | 3624 | 815 | 9 |
|   | WPSEL | 3832 | 1235 | 31 |
| 7 | UMSEL | 1180 | 158 | 0 |
|   | WPSEL | 1636 | 521 | 17 |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,672,035; U.S. Pat. No. 5,004,863; U.S. Pat. No. 5,159,135; U.S. Pat. No. 5,244,802, U.S. Pat. No. 5,583,036, U.S. Pat. No. 5,695,999;
Fraley et al., *Proc. Natl. Acad. Sci. USA*, 80:4803-4807, 1987.
Gamborg et al., *Exp. Cell Res.*, 50:151, 1968.
Klee, et al., *Bio/Technology*, 3:637-642, 1985.
Lide et al., In: *CRC Handbook of Chemistry*, 1997.
McCown and Lloyd, *Hort. Science*, 16:453, 1981.
Murashige and Skoog, *Physiol. Plant*, 15:473-497, 1962.
Nitsch and Nitsch, *Science*, 163:85-87, 1969.
Perl et al., *Nature Biotechnology*, 14:624-628, 1996.
Potrykus, *Ann. Rev. Plant Physiol. Plant Mol. Biol.*, 42: 205, 1991.
Rogers et al., *Annu. Rev. Plant Physiol.*, 38:467-486, 1987a.
Rogers et al., *Methods Enzymol.*, 153:253-277, 1987b.
Schenk and Hildebrandt, *Can. J. Bot.*, 50:199-204, 1972.
Stewart and Hsu, *Planta*, 137:113-117, 1977.

What is claimed is:

1. A method of improving the efficiency of cotton plant regeneration comprising the steps of:
    (a) culturing cotton plant tissue on non-embryogenic callus induction medium to produce a callus;
    (b) culturing the callus on embryogenic callus induction and embryo formation medium to produce an embryo;
    (c) culturing the embryo on embryo maturation medium to produce a mature embryo;
    (d) culturing the mature embryo on embryo germination medium; and
    (e) obtaining a regenerated cotton plant from the mature embryo;
    wherein the method further comprises culturing the cotton plant tissue in the presence of increased ethylene during step (a) in which callus induction takes place and without increased ethylene during steps (b-d) during which embryogenesis and embryo maturation takes place.

2. The method of claim 1, wherein the cotton plant tissue is cultured on non-embryogenic callus induction medium that comprises calcium nitrate and potassium sulfate; reduced ammonium nitrate, calcium chloride, potassium nitrate, potassium iodide, and cobalt chloride as compared to that found in MS medium; and enhanced cupric sulfate and manganese sulfate as compared to that found in MS medium.

3. The method of claim 1, wherein the tissue comprises a cell that is transformed by a heterologous DNA sequence prior to step (b) or step (c).

4. The method of claim 3, wherein the transformed cell is selected on a medium comprising kanamycin, glyphosate, or glufosinate.

5. The method of claim 3, further comprising pre-soaking the tissue in a liquid medium for at least 1 hour prior to transformation.

6. The method of claim 5, wherein the liquid medium comprises the basal salts and carbohydrate components of MSO glucose medium.

7. The method of claim 5, wherein the tissue is a cotton hypocotyl or cotyledonary explant.

8. The method of claim 1, wherein the non-embryogenic callus induction medium comprises the basal salts component of WPSEL medium.

9. The method of claim 1 wherein the non-embryogenic callus induction medium is WPSEL medium.

10. The method of claim 1, wherein the method further comprises culturing the cotton tissue in a medium containing a brassinosteroid and wherein the brassinosteroid is brassinolide.

11. The method of claim 1, further comprising culturing the cotton callus and/or embryo in a low oxygen environment.

12. The method of claim 1, wherein the method further comprises culturing the cotton callus and/or embryo in an atmosphere with altered air composition, and wherein the atmosphere is supplemented with one or more gases selected from a group consisting of ethylene, nitrogen, and carbon dioxide.

13. The method of claim 1, wherein the callus and/or embryo is cultured in a medium supplemented with one or more compound selected from the group consisting of: a Brassinosteroid, ethylene and an ethylene precursor.

14. The method of claim 1, comprising culturing the cotton plant tissue in a medium containing a brassinosteroid.

15. The method of claim 1, comprising culturing the cotton callus and/or embryo in an atmosphere with altered air composition.

16. The method of claim 1, comprising culturing the callus and/or embryo at a temperature of from 30° C. to about 34° C.

17. The method of claim 1, comprising culturing cotton plant tissue on non-embryogenic callus induction medium comprising ABA.

18. The method of claim 1, comprising culturing cotton plant tissue on non-embryogenic callus induction medium that comprises calcium nitrate and potassium sulfate; reduced ammonium nitrate, calcium chloride, potassium nitrate, potassium iodide, or cobalt chloride as compared to that found in MS medium; enhanced cupric sulfate and manganese sulfate as compared to that found in MS medium, or no potassium nitrate.

* * * * *